United States Patent [19]
de Juan, Jr. et al.

[11] Patent Number: 5,993,072
[45] Date of Patent: Nov. 30, 1999

[54] ADAPTER ASSEMBLY FOR CONNECTING MULTIPLE OPTIC FIBER ILLUMINATED MICROSURGICAL INSTRUMENTS TO A SINGLE LIGHT SOURCE

[75] Inventors: Eugene de Juan, Jr., Phoenix, Md.; Gregg D. Scheller; Michael D. Auld, both of Chesterfield, Mo.; Dyson Hickingbotham, Marietta, Ga.

[73] Assignee: The Johns Hopkins University, Baltimore, Md.

[21] Appl. No.: 08/633,428

[22] Filed: Apr. 17, 1996

[51] Int. Cl.⁶ ....................................................... G02B 6/36
[52] U.S. Cl. ................... 385/78; 385/902; 606/15; 606/16
[58] Field of Search ................... 606/15, 16, 17; 385/77, 15, 53, 55, 59, 115, 116, 117, 901, 902

[56] References Cited

U.S. PATENT DOCUMENTS

| 4,499,899 | 2/1985 | Lyons, III | 128/305 |
| 4,539,976 | 9/1985 | Sharpe | 128/4 |
| 4,562,838 | 1/1986 | Walker | 128/303.14 |
| 4,759,348 | 7/1988 | Cawood | 128/6 |
| 4,878,487 | 11/1989 | Sinnett | 128/20 |
| 5,163,935 | 11/1992 | Black et al. | 606/7 |
| 5,498,260 | 3/1996 | Rink et al. | 606/16 |

*Primary Examiner*—Hung N. Ngo
*Attorney, Agent, or Firm*—Howell & Haferkamp, LC

[57] ABSTRACT

An assembly of connectors adapt multiple optic fiber illuminators of microsurgical instruments for use with a variety of different available light sources.

24 Claims, 2 Drawing Sheets

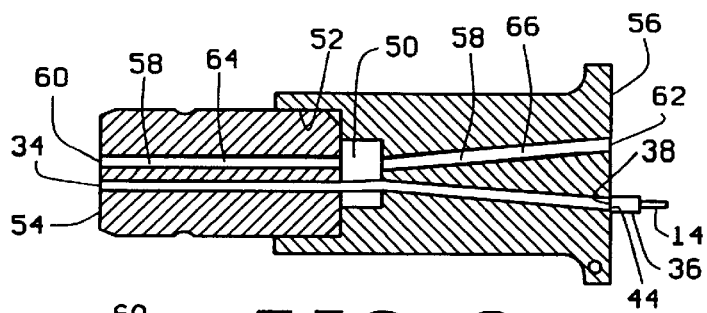
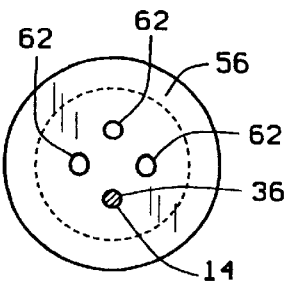
FIG.2  FIG.3
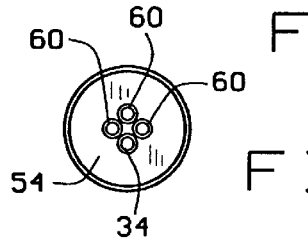
FIG.4
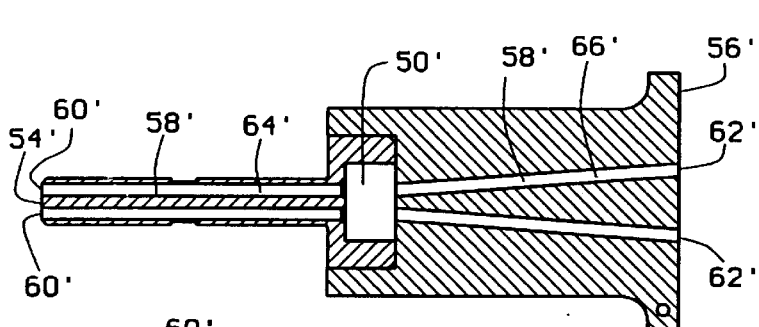
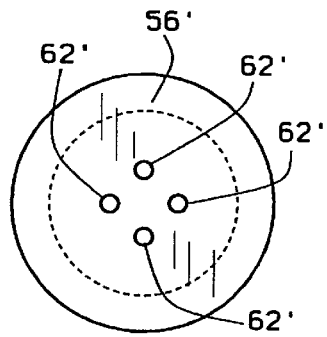
FIG.5  FIG.6
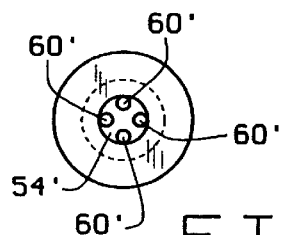
FIG.7
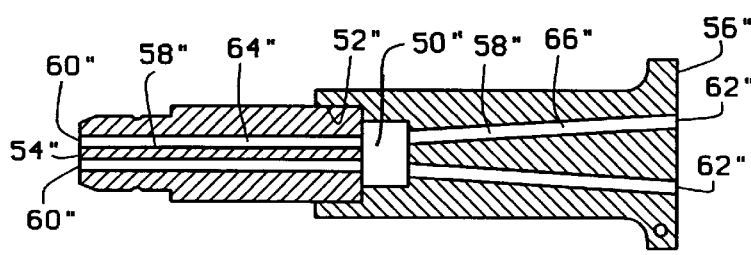
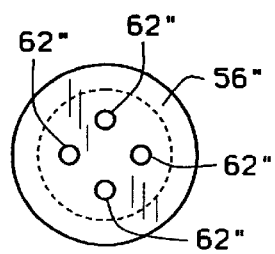
FIG.8  FIG.9
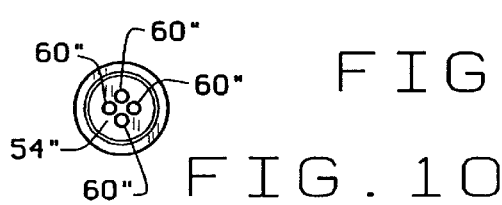
FIG.10

ADAPTER ASSEMBLY FOR CONNECTING MULTIPLE OPTIC FIBER ILLUMINATED MICROSURGICAL INSTRUMENTS TO A SINGLE LIGHT SOURCE

BACKGROUND OF THE INVENTION (1) Field of the Invention

The present invention pertains to an assembly of connectors that are used to adapt optic fiber illuminators of microsurgical instruments for use with a variety of different available light sources.

(2) Description of the Prior Art

In microsurgery such as ophthalmic surgery or surgery of the eye, various different types of instruments are available for use by the surgeon to illuminate the interior of the eye. These include a basic microsurgical illuminator that is comprised of a handle with a projecting tubular probe or tip and a length of optic fiber entering the rearward end of the handle and passing through the handle and tip to the tip distal end. By positioning a proximal end of the optic fiber adjacent a light source, the light is transmitted through the fiber to its distal end and is emitted from the distal end. In use of such an instrument in ophthalmic surgery, a small incision is first made in the eye and the probe tip is then inserted through the incision. The light transmitted through the probe by the optic fiber is emitted from the distal end of the probe and is used by the surgeon to illuminate the area of surgery in the interior of the eye.

Various other different types of instruments are available to the surgeon for illuminating the area of surgery in the interior of the eye. Many of these instruments also make use of a length of optic fiber to transmit illumination from a light source to the distal end of the surgical instrument where the light is needed.

There are many different manufacturers of light source apparatus that are used to illuminate optic fiber illuminated microsurgical instruments. Many manufacturers of microsurgical light sources also manufacture a set of optic fiber illuminated microsurgical instruments specifically adapted for use with their light source. This creates a situation where many optic fiber illuminated microsurgical instruments are suited for use with only one particular light source, the connector of the instruments being complementary to a connection of that one particular light source and not suited for use with light sources manufactured by competitors. Manufacturers have also provided adapter connectors that adapt the fiber optic connectors of other manufacturers for use with their light source, and to adapt their fiber optic connectors for use with the light sources of other manufacturers. However, production of these adapters requires their being machined to specific tolerances to match the connection of other manufacturers' light sources and fiber optic instruments. This is an expensive situation for the surgeon and the hospital, where a complete set of optic fiber illuminated surgical instruments must be available for use with each different type of optic fiber light source or adapter used by the surgeon or hospital.

What is needed to overcome this inconvenient and expensive situation is an inexpensive means of using any optic fiber illuminated microsurgical instrument available to the surgeon with any optic fiber illuminating light source available to the surgeon, and preferably to use a multiple of optic fiber instruments that are all simultaneously connectable to the same light source, thereby eliminating the expense of providing a separate light source for each instrument used.

SUMMARY OF THE INVENTION

It is an object of the present invention to provide an adapter assembly that includes a set of connectors, each connector of the set having a plug that is complementary configured for connection to a light emitting outlet of a commercially available light source, thereby providing a set of connectors, each of which is usable with a particular light source. Each of the connectors are also connectable with a variety of different optic fiber illuminated microsurgical instruments, preferably each connector being connectable to a multiple of instruments.

The adapter assembly of the present invention overcomes the inconvenience and expense associated with the use of many different optic fiber light sources by providing a set of connectors and instruments that may be used interchangably together to adapt the instruments for use with any commercially available light source, and where a multiple of the instruments may be simultaneously connected to the same light source. The adapter assembly of the invention includes a plurality of connector bases, each base having a plug thereon that is specifically configured for use in connecting the base with a light emitting connection of a particular one of a variety of different available optic fiber light sources. Each base also includes a plurality of fiber passages extending through the base, each being specifically designed to receive and hold the proximal end of an optic fiber illuminated instrument to transmit light emitted from the light source through the optic fiber.

Each assembly also includes a plurality of different types of optic fiber illuminated microsurgical instruments, each instrument having an optic fiber passing therethrough, from a proximal end of the fiber positioned remote from the instrument to a distal end of the fiber positioned at a distal end of the instrument where light emitted from the fiber distal end will illuminate the area of surgery at which the instrument is being used. The proximal ends of each of the fibers are provided with the same straight, resilient sleeve surrounding the fiber and an abutment positioned at the end of the sleeve. The sleeve has a predetermined length corresponding to the length of each of the fiber passages passing through each of the connector bases. Inserting the resilient sleeve into one of the fiber passages of one of the bases positions the proximal end of the optic fiber at the proximal end of the base and adjacent the light source. Assembling the proximal end of the optic fiber into a fiber passage of a particular base, and then connecting the base to the available light source for which the base plug has been specifically configured adapts the optic fiber illuminated microsurgical instrument for illumination by any one of the variety of different available light sources.

BRIEF DESCRIPTION OF THE DRAWINGS

Further objects and features of the present invention are revealed in the following detailed description of the preferred embodiment of the invention and in the drawing figures wherein:

FIG. 2 is a side elevation view, in section, of one connector base of the plurality of connector bases that make up the assembly of the invention;

FIG. 3 is a distal end elevation view of the base of FIG. 2;

FIG. 4 is a proximal end elevation view of the base of FIG. 2;

FIG. 5 is a side elevation view, in section, of an additional base of the assembly of the invention;

FIG. 6 is a distal end elevation view of the base of FIG. 5;

FIG. 7 is a proximal end elevation view of the base of FIG. 5;

FIG. 8 is a side elevation view, in section, of a further base of the assembly of the invention;

FIG. 9 is a distal end elevation view of the base of FIG. 8; and

FIG. 10 is a proximal end elevation view of the base of FIG. 8.

DESCRIPTION OF THE PREFERRED EMBODIMENT

Figure 1:
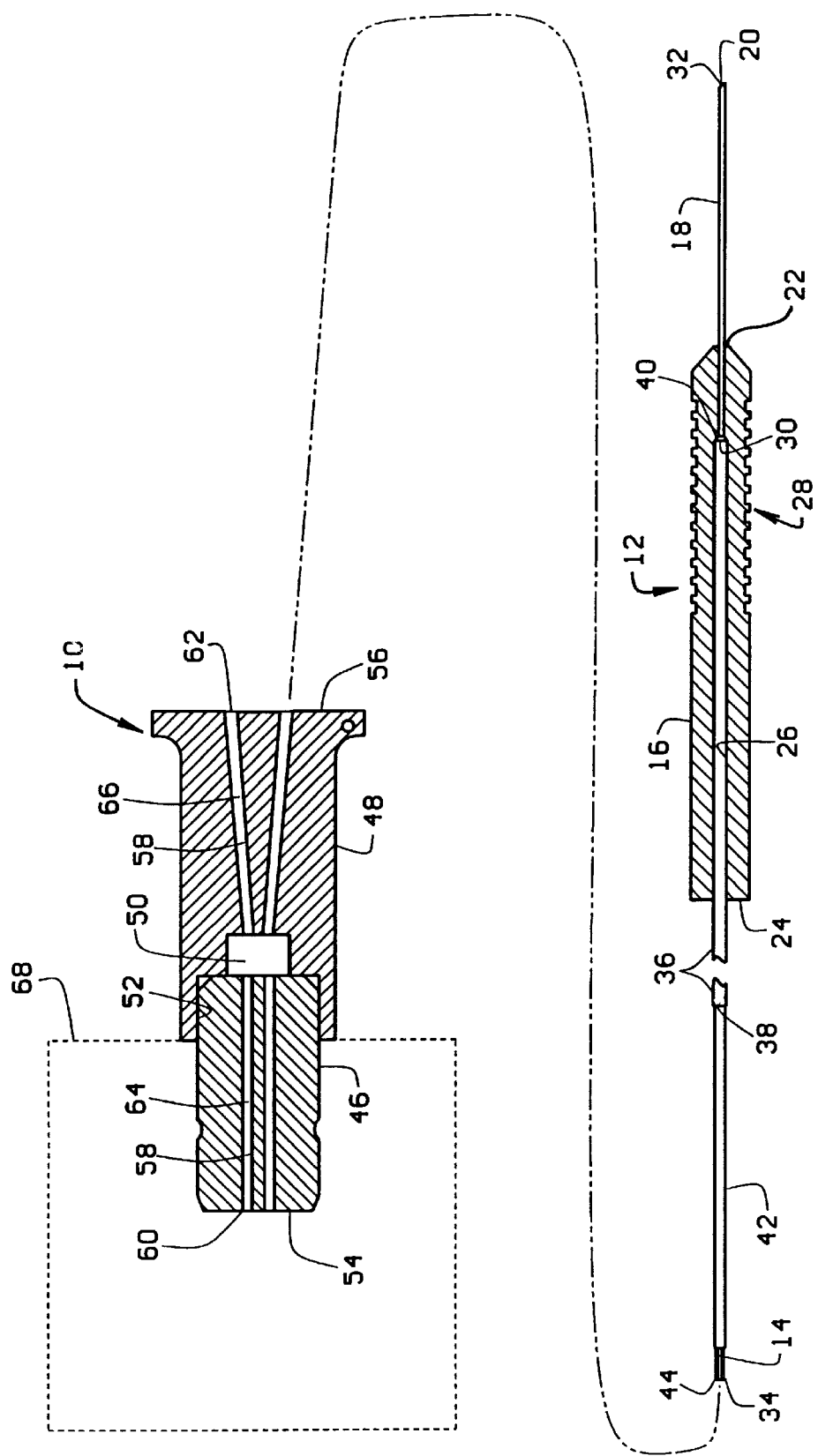
FIG. 1 is a fragmented side elevation view, partially in section, of the microsurgical illuminator assembly of the present invention.

The adapter assembly of the invention is used in connecting various different optic fiber illuminated microsurgical instruments to a variety of different light sources. The assembly is comprised of a plurality of different connector bases (in the illustrative embodiment of the assembly three different bases are described), and a plurality of different optic fiber illuminated microsurgical instruments (in the illustrative embodiment an ophthalmic surgery illuminator probe is described). However, it should be understood that the adapter assembly of the invention may comprise as many different connector bases as there are commercially available light sources for use in illuminating optic fibers, and the number of microsurgical instruments employed with the plurality of connector bases may comprise every available instrument in which light is conveyed to the operative end of the instrument by an optic fiber. Although only three connector bases are described in the description to follow and only one microsurgical instrument is described, it is not intended that the assembly of the invention be limited to only three bases and one instrument. Furthermore, although an illuminator probe used in ophthalmic surgery is described as the surgical instrument employed with the plurality of connector bases of the assembly, different types of ophthalmic instruments such as the tissue manipulator disclosed in the Sinnett U.S. Pat. No. 4,878,487, may be employed in the assembly of the invention, as well as other microsurgical instruments used in other than eye surgery such as the microsurgical scissors disclosed in the Lyons U.S. Pat. No. 4,499,899.

With reference to FIG. 1, the adapter assembly used in connecting the optic fiber of a microsurgical instrument to a light source basically comprises a plurality of connector bases 10, a plurality of microsurgical instruments 12 (only one of which is shown), each instrument having a length of optic fiber 14 connecting the instrument to the base.

The surgical instrument 12 used in this illustrative embodiment of the invention is a microsurgical illuminator that is primarily used in ophthalmic or eye surgery. The illuminator is basically comprised of a handle 16, a cannula tip or probe 18 projecting from the handle, and the distal end 20 of the optic fiber 14 that extends through the handle and probe.

The handle 16 is elongated and has opposite distal 22 and proximal 24 ends. A center bore 26 having a enter axis extends through the interior of the handle between its opposite ends. The exterior surface of the handle has a circumferential dimension approximately that of a pen or pencil, providing a familiar and comfortable feel to the surgeon's hand when holding the handle. A portion 28 of the handle exterior surface is ribbed or grooved, providing a gripping surface.

The cannula tip or probe 18 is a rigid, tubular sleeve preferably constructed of surgical steel. The probe also has an interior bore with a center axis that is coaxial to the interior bore of a handle. A proximal end 30 of the probe is received in the interior bore of the handle at the handle distal end and is securely held therein. The probe projects axially from the handle distal end 22 for a significant portion of its length to a distal end 32 of the probe.

The optic fiber 14 employed in the preferred embodiment of the assembly is a single strand optic fiber, although a bundle of fibers may also be employed in lieu of the single fiber. Therefore, "optic fiber" as used herein is intended to include a single fiber or a bundle of fibers. The fiber has a significant length so that the surgeon is not encumbered when using the instrument connected to the distal end of the fiber. The fiber extends from its distal end 20 in the probe tip to a proximal end 34 remote from the instrument. A flexible opaque tubing 36 surrounds the fiber and extends along the fiber from a proximal end 38 of the tubing adjacent the fiber proximal end 34, to a distal end 40 of the tubing adjacent the fiber distal end 20. As shown in FIG. 1, the tubing distal end 40 ends in the interior of the handle 16 and the optic fiber projects beyond the tubing distal end 40 through the probe 18 and terminates at a planar surface at the distal end of the optic fiber that is substantially coplanar with the annular distal end surface of the probe 18. The proximal end 38 of the tubing ends adjacent the fiber proximal end 34, but does not extend to the fiber proximal end. Instead, a portion of the optic fiber adjacent its proximal end 34 is contained in a flexible, resilient sleeve 42 that is secured to the tubing proximal end 38 by adhesive or other equivalent methods.

In the preferred embodiment, the sleeve is constructed of surgical steel, but may be constructed of other materials having sufficient rigidity to protect the optic fiber proximal end 38, but also sufficient flexibility and resiliency for the purposes yet to be explained. The optic fiber extends beyond the tubing proximal end 38 through the interior of the sleeve 42 to the proximal end surface of the fiber 34 positioned substantially coplanar with the annular proximal end surface 44 of the sleeve. In an alternate embodiment, the sleeve 42 may be removed leaving the bare optic fiber projecting from the tubing proximal end. In this embodiment the resilience of the bare optic fiber serves the purpose of the sleeve yet to be explained.

As seen in FIG. 1, where the proximal end of the tubing 38 joins the distal end of the sleeve 42, the tubing forms an annular abutment that extends radially beyond the sleeve. The purpose of this abutment will be explained. However, it should be understood that the abutment formed by the tubing proximal end 38 may be replaced by other similar types of abutments, for example a protrusion on the exterior surface of the sleeve 42 at its distal end where it joins the tubing. Either of these types of abutments, or other similar abutments, will be equally well-suited for performing the function of the abutment yet to be explained.

As stated earlier, the assembly of the invention is also comprised of a plurality of connector bases, one of which is shown in FIGS. 1–4. Referring first to FIG. 1, the connector base 10 shown in comprised of two sections, a first proximal section 46 and a second distal section 48. The two-section construction of the base permits the positioning of a hollow, central cavity 50 at the interior of the base. The cavity 50 has a cylindrical interior surface configuration machined in the base second or distal section 48. The cavity may also be machined in the base first section. A larger cylindrical interior cavity 52 is also machined in the interior of the base second section 48. However, this cavity contains the base proximal section 46 as shown in FIGS. 1 and 2. A portion of the base proximal section 46 is inserted into the larger cavity 52 and is secured therein by welding, brazing or other equivalent methods. Connecting the two base sections together in this manner secludes the central cavity 50 in the base interior.

The base is formed with opposite proximal 54 and distal 56 end surfaces and a plurality of fiber passages 58 extending through the base interior between these surfaces. In the illustrative embodiment, four fiber passages 58 extend through the interior of the base enabling as many as four instrument optic fibers 14 to be connected to the base. Each fiber passage has a proximal opening 60 in the proximal end surface 54 of the base and a distal opening 62 in the distal end surface of the base. Each of the fiber passages 54 are dimensioned to receive the flexible sleeve 42 at the proximal ends of the instrument optic fiber 14. The length of the fiber passages 54 corresponds to the length of the sleeve 42 so that the abutment formed by the fiber tubing proximal end 38 engages against the base distal surface 56 when the sleeve is inserted through the fiber passage to the extent that the sleeve proximal end and the optic fiber proximal end 34 are positioned in the proximal opening 60 of the fiber passage 58 in the same plane as the base connector proximal surface 54.

Each of the fiber passages 54 passing through a connector base 10 is comprised of a first section 64 of the passage passing through the base proximal section 46, and a second section 66 of the passage passing through the base distal section 48. The first and second fiber passage sections are oriented at an angle to each other so that each fiber passage deviates from a straight line as it passes through the base. This also positions the proximal opening 60 of the fiber passages closer to each other at the base proximal surface 54 than the fiber passage distal opening 62 at the base distal surface 56. The central cavity 50 of the base separates the fiber passage first section 64 from the fiber passage second section 66.

The relative positions of the fiber passage first and second sections and of the central cavity of the base serve several purposes. On inserting the resilient sleeve 42 of the instrument optic fiber into a fiber passage from its distal opening 62, the second section 66 of the fiber passage directs the sleeve to the central cavity 50. The orientation of the fiber passage second section 66 also directs the sleeve at the proximal end 34 of the optic fiber across the central cavity 50 and into the fiber passage first section 64. As the sleeve progresses through the fiber passage first section 64, the difference in orientation between the first section 64 and second section 66 of the fiber passage deviates or slightly bends the sleeve. The sleeve is continued to be pushed through the first and second sections of the fiber passage 58 until the abutment formed by the tubing proximal end 38 engages against the base distal surface 56, thereby preventing further insertion of the sleeve into the fiber passage. In this position of the sleeve, the proximal end 34 of the fiber is positioned in the same plane as the base proximal surface 54 in the proximal opening 60 of the fiber passage. The bend formed in the sleeve 42 by the angled orientation of the fiber passage first and second sections, 64, 66 serves to hold the sleeve in the fiber passage against the unintentional pulling of the sleeve from the passage. In order to now remove the sleeve from the passage, some force must be exerted on the sleeve by the user's hand to pull the sleeve from the passage.

Additionally, the angled orientation of the two fiber passage sections positions the distal openings 62 of the fiber passages further apart from each other than the proximal openings 60 of the passages. Should several optic fiber sleeves be inserted in the fiber passages of a single base, the additional spacing providing by the distal opening 62 of the fiber passages permits one of the optic fibers to be easily grasped between the fingers of a user's hand to remove or insert the fiber sleeve without interference from the other fibers inserted into the fiber passages of the connector base.

When a fiber sleeve 42 is removed from a passage, the angled orientation of the two passage sections acts as a light shutter, limiting the amount of light and glare escaping through the open passage.

Still further, the central cavity 50 provided in the connector base interior between the two fiber passage sections provides an area where the sleeve may bend between the two straight line sections of the sleeve contained in the first and second sections of the passages. Providing the central cavity 50 at this area of deviation of the optic fiber sleeve prevents the sleeve from crimping as it is inserted through the fiber passages.

The exterior surface of the base proximal section 46 is the only thing that differs between each base and each is formed in the configuration of a plug complementary to the light emitting opening of a particular available light source 68. It is a principle feature of the assembly of the invention to provide a set of a plurality of connector bases, the exterior surfaces of the proximal section 46 of each base forming a connector plug that is complementary to the light emitting opening of a particular commercially available light source. With such a set of connector bases 10, a connector base is provided that may be removably attached to the light emitting opening of each of the commercially available sources of light. To further illustrate this feature of the invention, FIGS. 5–7 and FIGS. 8–10 show two additional connector bases having proximal sections with exterior surfaces configured complementary to a light emitting opening of a commercially available light source. In these drawing figures, features of the connector bases similar to those of the base connector shown in FIGS. 1–4 are given like reference numerals followed by a prime (') in FIGS. 5–7 and a double prime (") in FIGS. 8–10. The resilient sleeve(s) 42 of one or more instrument optic fiber(s) may be inserted into and removably held by the fiber passages 58 of each of these additional connector bases, and the proximal sections 46 of each of these connector bases may be inserted into a light emitting opening of a particular commercially available source of light to removably connect the connector base to the source of light.

In an alternative embodiment, the connector base may be a permanently attached part of a particular light source.

In the above-described manner, the assembly of the invention may be used to connect a multiple of optic fiber illuminated surgical instruments to any one of a variety of different commercially available light sources. Furthermore, should other light sources having new light emitting openings be made available, a complementary configured base connector may be added to the set of base connectors of the assembly of the invention to adapt the surgical instruments of the assembly of the invention for use with this newly introduced light source.

While the present invention has been described by reference to a specific embodiment, it should be understood that modifications and variations of the invention may be constructed without departing from the scope of the invention defined in the following claims.

What is claimed:

1. An adapter assembly used in connecting optic fibers to a light emitting outlet of a light source to transmit emitted light through the optic fibers, the assembly comprising:

a connector base having opposite proximal and distal ends, the base proximal end connecting the base to the light emitting outlet of the light source;

a plurality of fiber passages passing through the base between the proximal end and the distal end, each of the fiber passages having a proximal opening at the base proximal end and a distal opening at the base distal end; and, a plurality of optic fibers, each optic fiber having opposite proximal and distal ends with the proximal end of each fiber being removably inserted in one of the base fiber passages and the distal end of each fiber being connected to a surgical instrument.

2. The assembly of claim 1, wherein:

the base includes a plug that is configured complementary to the light emitting outlet for being removably press fit to the outlet.

3. The assembly of claim 1, wherein:

each fiber passage passing through the base has a first section adjacent the base proximal end and a second section adjacent the base distal end, the first and second sections each have a center axis and the axes of the first and second sections are oriented at an angle to each other.

4. The assembly of claim 3, wherein:

the base has a central open cavity in its interior and the first and second sections of each of the fiber passages are separated by the cavity.

5. The assembly of claim 1, wherein:

each fiber passage passing through the base has a first section adjacent the base proximal end and a second section adjacent the base distal end, and the base has an interior open cavity that separates the first and second sections of each of the fiber passages.

6. The assembly of claim 1, wherein:

the proximal openings of the plurality of fiber passages are positioned closer to each other on the base proximal end than are the distal openings of the plurality of fiber passages on the base distal end.

7. The assembly of claim 1, wherein:

the proximal end of each optic fiber has a configuration for permitting insertion of the fiber proximal end through any one of the plurality of fiber passages.

8. The assembly of claim 1, wherein:

the proximal end of each optic fiber is configured for removably inserting the fiber proximal end through each base fiber passage from the distal opening of each fiber passage until the fiber proximal end reaches the proximal opening of each fiber passage and then prevents further insertion of the proximal end through each fiber passage.

9. The assembly of claim 1, wherein:

each optic fiber has an exterior surface with an abutment thereon that is spaced from both the proximal end and the distal end of the optic fiber, and the spacing of the abutment from the fiber proximal end corresponds to a length of each fiber passage between its distal opening and proximal opening so that the abutment of each optic fiber will engage against the base distal end when the fiber proximal end is positioned in the proximal opening of each fiber passage.

10. The assembly of claim 1, wherein:

each fiber passage deviates from a straight line path as it extends through the base from the base distal end to the base proximal end.

11. The assembly of claim 10, wherein:

each optic fiber has a straight configuration adjacent its proximal end that is deviated by the base fiber passage as the fiber proximal end is inserted through the fiber passage, the deviation of the fiber proximal end by the fiber passage serving to hold he fiber proximal end in the fiber passage.

12. The assembly of claim 11, wherein:

each optic fiber is contained in a straight, resilient sleeve at its proximal end, the sleeve bends as it is inserted into one of the fiber passages and returns to its straight configuration as it is removed from the fiber passage.

13. The assembly of claim 1, wherein:

the base is one of a plurality of bases, each having opposite proximal and distal ends and each having a plurality of fiber passages extending between the proximal and distal ends, and each base having means for removably connecting the base to a specifically configured light emitting outlet of a light source with each means being different from the other means of the plurality of bases.

14. An adapter assembly used in connecting optic fibers to a light emitting outlet of a light source to transmit emitted light through the optic fibers, the assembly comprising:

a connector base having opposite proximal and distal ends, the base proximal end having means for removably connecting the base to the light emitting outlet of the light source;

at least one fiber passage passing through the base between the proximal end and the distal end, the fiber passage having a proximal opening at the base proximal end and a distal opening at the base distal end; and at least one optic fiber having opposite proximal and distal ends with the proximal end of the fiber being removably inserted in the base fiber passage and the distal end of the fiber being connected to a surgical instrument.

15. An adapter assembly used in connecting optic fibers to a light emitting outlet of a light source to transmit emitted light through the optic fibers, the assembly comprising:

a connector base having opposite proximal and distal ends, the base proximal end having means for removably connecting the base to the light emitting outlet of the light source;

at least one fiber passage passing through the base between the proximal end and the distal end, the fiber passage having a proximal opening at the base proximal end and a distal opening at the base distal end;

at least one optic fiber having opposite proximal and distal ends with the proximal end of the fiber being removably inserted in the base fiber passage and the distal end of the fiber being connected to a surgical instrument; and the base is one of a plurality of bases, each having opposite proximal and distal ends and each having the same fiber passage passing through the base between the opposite proximal and distal ends, and each base differing from other bases of the plurality by having different means for removably connecting the base to a light emitting outlet of a light source.

16. An adapter assembly used in connecting optic fibers to a light emitting outlet of a light source to transmit emitted light through the optic fibers, the assembly comprising:

a connector base having opposite proximal and distal ends, the base proximal end having means for removably connecting the base to the light emitting outlet of the light source;

at least one fiber passage passing through the base between the proximal end and the distal end, the fiber passage having a proximal opening at the base proximal end and a distal opening at the base distal end;

at least one optic fiber having opposite proximal and distal ends with the proximal end of the fiber being removably inserted in the base fiber passage and the distal end of the fiber being connected to a surgical instrument; and the fiber passage is one of a plurality of fiber passages passing through the base between its proximal and distal ends, each of the fiber passages having a proximal opening at the base proximal end and a distal opening at the base distal end; and the optic fiber is one of a plurality of optic fibers, each having opposite proximal and distal ends with the proximal end of each fiber being removably inserted in one of the base fiber passages and the distal end of each fiber being connected to a surgical instrument.

17. The assembly of claim 14, wherein:

the fiber passage has a first section adjacent the base proximal end and a second section adjacent the base distal end, the first and second sections each have a center axis and the axes of the first and second sections are oriented at an angle relative to each other.

18. The assembly of claim 17, wherein:

the base has an interior cavity that separates the first and second sections of the fiber passage.

19. The assembly of claim 14, wherein:

the fiber passage has a first section adjacent the base proximal end and a second section adjacent the base distal end, and the base has an interior cavity that separates the first and second sections.

20. The assembly of claim 14, wherein:

the proximal end of the optic fiber is configured for insertion into the fiber passage from the distal opening until the fiber proximal end reaches the proximal opening of the fiber passage and then prevents further insertion of the optic fiber.

21. The assembly of claim 1, wherein:

the optic fiber has an exterior surface with an abutment thereon that is spaced from the proximal end and distal end of the fiber, the spacing of the abutment from the fiber proximal end corresponds to a length of the fiber passage between the distal opening and proximal opening so that the abutment will engage against the base distal end when the fiber proximal end is positioned in the proximal opening of the fiber passage.

22. The assembly of claim 14, wherein:

the fiber passage deviates from a straight line path as it extends from the distal opening to the proximal opening.

23. An adapter assembly used in connecting optic fibers to a light emitting outlet of a light source to transmit emitted light through the optic fibers, the assembly comprising:

a connector base having opposite proximal and distal ends, the base proximal end having means for removably connecting the base to the light emitting outlet of the light source;

at least one fiber passage passing through the base between the proximal end and the distal end, the fiber passage having a proximal opening at the base proximal end and a distal opening at the base distal end;

at least one optic fiber having opposite proximal and distal ends with the proximal end of the fiber being removably inserted in the base fiber passage and the distal end of the fiber being connected to a surgical instrument; and the fiber passage deviates from a straight line path as it extends from the distal opening to the proximal opening; and the optic fiber has a straight configuration adjacent its proximal end that is bent by the base fiber passage as the fiber proximal end is inserted through the fiber passage, the bending of the fiber proximal end by the fiber passage serving to hold the fiber proximal end in the fiber passage.

24. The assembly of claim 23, wherein:

the optic fiber is contained in a straight, resilient sleeve at its proximal end, the sleeve bends as it is inserted into the fiber passage of the base and returns to its straight configuration as it is removed from the fiber passage.

* * * * *